United States Patent
Ikemoto et al.

(10) Patent No.: US 6,576,247 B1
(45) Date of Patent: Jun. 10, 2003

(54) SUSTAINED-RELEASE AROMATIC AND METHOD OF DETECTING MICRO-ORGANISM BY USING THE SAME

(75) Inventors: Takeshi Ikemoto, Kanagawa (JP); Hiroko Nakatsugawa, Kanagawa (JP); Bun-ichi Okabe, Kanagawa (JP); Kazuo Ogino, Tokyo (JP); Jun-ichi Matsui, Kanagawa (JP); Minoru Iwamoto, Kanagawa (JP); Akira Fujita, Kanagawa (JP); Masayoshi Inui, deceased, late of Kanagawa (JP), by Sachiko Inui, Toshihiro Invi, Masami Inui and Masayuki Inui, legal representatives

(73) Assignee: Kanebo Ltd. and T. Hasegawa Co. Ltd. (JP)

( * ) Notice: Subject to any disclaimer, the term of this patent is extended or adjusted under 35 U.S.C. 154(b) by 0 days.

(21) Appl. No.: 08/849,421

(22) PCT Filed: May 10, 1995

(86) PCT No.: PCT/JP95/00898
  § 371 (c)(1),
  (2), (4) Date: Mar. 8, 1999

(87) PCT Pub. No.: WO96/14827
  PCT Pub. Date: May 23, 1996

(30) Foreign Application Priority Data

Nov. 10, 1994 (JP) ............................. 6-303204
Feb. 17, 1995 (JP) ............................. 7-053533
Apr. 18, 1995 (JP) ............................. 7-117756

(51) Int. Cl.$^7$ ............................. A61K 7/00; A61K 7/32; A61K 7/06; A61K 7/46
(52) U.S. Cl. ............................. 424/401; 424/65; 424/70.1; 512/1
(58) Field of Search ............................. 424/401, 65, 70.1; 512/1

(56) References Cited

U.S. PATENT DOCUMENTS

| | | |
|---|---|---|
| 3,988,482 A | 10/1976 | Higashiyama et al. |
| 4,038,270 A | 7/1977 | Higashiyama et al. |
| 4,157,384 A * | 6/1979 | Watson et al. ............... 424/45 |

(List continued on next page.)

FOREIGN PATENT DOCUMENTS

| | | |
|---|---|---|
| DE | 37 18 340 A1 | 12/1988 |
| JP | 50(1975)-63145 | 5/1975 |
| JP | 50(1975)-82104 | 7/1975 |
| JP | 55(1980)-133306 | 4/1979 |
| JP | 62-283992 | 12/1987 |
| JP | 02196795 A * | 8/1990 |
| JP | 3-17025 | 1/1991 |
| JP | 3-90016 | 4/1991 |
| JP | 3-287597 | 12/1991 |
| JP | 4-170961 | 6/1992 |
| JP | 4-300889 | 10/1992 |
| JP | 5-230496 | 9/1993 |
| JP | 5-239491 | 9/1993 |
| JP | 6057288 | 3/1994 |
| JP | 0636401 A * | 12/1994 |
| WO | WO 94/06441 | 3/1994 |
| WO | WO 94/11015 | 5/1994 |
| WO | WO 95/08976 | 4/1995 |

OTHER PUBLICATIONS

V. Jo Davisson et al., "Synthesis of Allylic and Homoallylic Isoprenoid Pyrophosphates," *Methods in Enzymology*, 1985, 110, pp. 130–144.

D. Drider et al., "Enzymatic Hydrolysis of Monoterpene Glycosides of Passion Fruit and Mango With a β–Glucosidase From Yeast," *Bioresource Technology*, 1994, vol. 49, pp. 243–246.

Denis Dubourdieu et al., "Rôle de la Levure *Saccharomyces Cerevisiae* dans l'Hydrolyse Enzymatique des Hétérosides Terpéniques du Jus de Raisin," *Comptes Rendus de L'Académie des Sciences de Paris*, vol. 306, Serie III Sciences de la Vie, No. 15, Apr. 21, 1988, pp. 489–493. ("Role of the Yeast *Sacchomyces Cerevisiae* in Enzymatic Hydrolysis of Terpenic Heterosides of Grape Fruit," Abstract in English on p. 489).

A. C. Hayward, "Occurence of Glycoside Hydrolases in Plant Pathogenic and Related Bacteria," *The Journal of Applied Bacteriology*, Dec. 1977, vol. 43, No. 3, Published for the Society for Applied Bacteriology by Academic Press, pp. 407–411.

(List continued on next page.)

*Primary Examiner*—Jose G. Dees
*Assistant Examiner*—Marina Lamm
(74) *Attorney, Agent, or Firm*—Townsend and Townsend and Crew LLP

(57) ABSTRACT

The present invention provides a sustained-release aromatic, characterized in that the aromatic comprises at least one perfume derivative as an active component selected from glycosides of perfumes, phosphoric acid ester derivatives of perfumes, amino acid derivatives of perfumes and carboxylic acid derivatives of perfumes, and contains no enzyme or acid which decomposes the perfume derivative, wherein the perfume derivative is decomposed by bacteria usually present on the skin or yeast to release a perfume component to exhibit aroma. The present invention also provides a method for the detection of micro-organisms using the aforesaid sustained-release aromatic. As the sustained-release aromatic of the present invention releases a perfume component only when it is decomposed by micro-organisms such as bacteria usually present on the skin or yeast, the amount of perfumes to be used can be extremely reduced. The sustained-release aromatic of the present invention is also excellent in keeping aroma. The stability with the passage of time of the sustained-release aromatic of the present invention is much better than that of the prior art because the perfume component is contained in the form of derivative. The sustained-release aromatic of the present invention is useful for applications on the skin, head skin or hair of human beings or animals, on clothes, or in drinks and foods, or as an indicator for detecting micro-organisms.

16 Claims, No Drawings

U.S. PATENT DOCUMENTS

| | | | |
|---|---|---|---|
| 4,431,576 A | * 2/1984 | Martel et al. | ................ 252/522 |
| 4,714,565 A | 12/1987 | Wevers et al. | |
| 4,804,002 A | * 2/1989 | Herron | ....................... 131/365 |
| 5,081,111 A | 1/1992 | Akimoto et al. | |
| 5,271,419 A | * 12/1993 | Arzonico et al. | ........... 131/365 |
| 5,320,837 A | 6/1994 | Akimoto et al. | |
| 5,378,468 A | * 1/1995 | Suffis et al. | ................ 424/401 |
| 5,649,979 A | 7/1997 | Paget et al. | |
| 5,726,345 A | 3/1998 | Paget et al. | |

OTHER PUBLICATIONS

Wilhelm Koenigs und Eduard Knorr, "Ueber Einige Derivate des Traubenzuckers und der Galactose," *Berichte der Deutschen Chemischen Gesellschaft*, 1901, vol. 34, pp. 957–981. (Partial English Translation included, 6 pages).

A translated copy of the Abstract of Japanese Application No. 04-043461, Sep. 1993.

A translated copy of the Abstract of Japanese Application No. 61-123774, Dec. 1987.

A translated copy of the Abstract of Japanese Application No. 01-225766, Apr. 1991.

A translated copy of the Abstract of Japanese Application No. 02-086631, Dec. 1991.

A translated copy of a portion of Japanese Application No. 51-105, May 1976.

* cited by examiner

SUSTAINED-RELEASE AROMATIC AND METHOD OF DETECTING MICROORGANISM BY USING THE SAME

FIELD

The present invention relates to a sustained-release aromatic comprising a gradually releasable perfume derivative. The present invention particularly relates to a sustained-release aromatic comprising a gradually releasable perfume derivative which is decomposed by micro-organisms to release an aroma component, and to a method for the detection of micro-organisms by the sustained-release aromatic.

PRIOR ART

Various methods has been used in the prior art to blend perfumes in a sustained-release aromatic composition, such as cosmetics, e.g. hair liquids, hair mousses and antiperspirant agents, room aromatics and drinks and foods. For example, in liquid products use have been made of water-solublilized perfumes obtained by dissolving oily perfumes in a solvent or carrier such as alcohols, propylene glycol, carbitol, etc. Alternatively, oily perfumes have been solubilized or emulsified in liquid or creamy products by the use of a surfactant. In powdery or solid products, these oily perfumes has generally been blended as powder or granule made by means of adsorption, capsulation or coating with the aid of a proper excipient, or as a clathrate compound.

Perfumes added to a sustained-release aromatic composition in the prior art have a problem that they start to be released immediately after applied to, for example, a human body and is quickly lost with the passage of time. In order to prevent such too quick diffusion of aroma, carriers are added. However, this method was insufficient in the effect. The perfumes added as a clathrate compound or a capsulated material are excellent in keeping the perfumes, but not too much excellent to emit aroma. Accordingly, they are not always satisfactory as a perfume-carrying material. Thus, there has been a strong desire for a sustained-release aromatic composition which stably generates aroma to a proper extent over a long time.

In order to solve this problem, there has been proposed an aromatic composition comprising an enzyme or acid and a derivative of a perfume which decomposes by the action of the enzyme or acid to form a perfume (e.g. glycosides or glycerides of a perfume, or amino acid or peptide derivatives of a perfume) (Japanese Patent Application Laid-Open Nos. Hei-4-170961/92, Hei-5-230496/93 and Hei-5-239491193). However, in the aromatic composition comprising an acid, it is necessary to blend the acid at a high concentration in the composition. This, therefore, causes a problem of safety when it is put on the skin.

There has also been proposed an oral composition in which at least one glycoside selected from thymol glycosides, cis-3-hexenol glycosides and methyl salicylate glycosides is added (Japanese Patent Application Laid-Open No. Hei-3-90016/91). When the composition is used, the glycoside is hydrolyzed by the action of glucosidase in saliva to release thymol, cis-3-hexenol or methyl salicylate, respectively, and exhibit flavor.

In addition to the aforesaid glycosides, there are known glycosides of mono-terpenes, such as perillyl alcohol, which are present in natural plants and can be synthesized easily and which exhibit pharmacological activity in cooperation with other components (Japanese Patent Application Laid-Open Nos. Hei-3-287597/91 and Hei-4-300889/92). However, the aforesaid publications do not refer to its aromatic effect.

An agent which gradually releases active components has also been proposed. This is an ester of a polyvalent alcohol having a carboxylic group or an oxyalkylene derivative of a polycarboxylic acid with a hydroxide group-containing active component (Japanese Patent Application Laid-Open No. Hei-3-17025/91). However, because the molecular weight of the polyvalent alcohol or the oxyalkylene derivative is relatively high, a ratio of aromatic components contained as the active component is small. Accordingly, it is unsatisfactory in an extent of aroma. In addition, as the aforesaid agent generates the active components as a result of hydrolysis, it is poor in stability during storage for a long period. This leads to a problem that aroma decreases with the passage of time.

DISCLOSURE OF THE INVENTION

A purpose of the present invention is to provide a sustained-release aromatic which is excellent in keeping aroma and a method for the detection of micro-organism using the same.

The present inventors have made researches to provide a sustained-release aromatic which stably generates aroma to a proper extent over a long time. As a result, we have found that when a perfume derivative selected from glycosides, phosphate ester derivatives, amino acid derivatives and carboxylic acid derivatives of perfume components is put on the skin, the perfume derivative itself releases very weak aroma, but it is decomposed by bacteria usually present on the skin to generate perfume components and the gradual decomposition by bacteria provides stable release of aroma over a long time. It has further been found that it does not happen that aroma decreases quickly with the passage of time by increased decomposition of the perfume derivative with propagation of these bacteria usually present on the skin which are safe for organisms. In addition, it has been found that as yeast also gradually decomposes the aforesaid perfume derivative, aroma is released stably over a long time.

The perfume derivatives contained in the sustained-release aromatic of the invention have no aroma or extremely weak aroma in themselves. Accordingly, it is possible to detect the presence and propagation of micro-organism such as bacteria usually present on the skin or yeast using the sustained-release aromatic of the invention by detecting the released aroma.

The present invention provides a sustained-release aromatic, characterized in that the aromatic comprises at least one perfume derivative as an active component selected from glycosides of perfumes, phosphoric acid ester derivatives of perfumes, amino acid derivatives of perfumes and carboxylic acid derivatives of perfumes, and contains no enzyme or acid which decomposes the perfume derivative, wherein the perfume derivative is decomposed by bacteria usually present on the skin or yeast to release a perfume component to exhibit aroma.

The present invention also provides a method for the detection of micro-organisms, characterized by use of a sustained-release aromatic comprising at least one perfume derivative as an active component selected from glycosides of perfumes, phosphoric acid ester derivatives of perfumes, amino acid derivatives of perfumes and carboxylic acid derivatives of perfumes, wherein the perfume derivative is decomposed by a micro-organism to diffuse aroma which is then detected.

The sustained-release aromatic of the present invention comprises a perfume derivative which is not volatile, or less volatile, compared to a perfume, and a volatile perfume is released gradually by the action of micro-organisms only after it is put into use. Accordingly, the perfume derivative is not decomposed during storage before it is used and, therefore, is excellent in a long time stability. The sustained-release aromatic of the present invention does not contain any enzyme nor acid which decomposes the aforesaid perfume derivative to release the perfume.

Meanwhile, the invention disclosed in Japanese Patent Application Laid-Open No. Hei-4-170961192 provides an aromatic composition which comprises a blended perfume comprising at least each one of top note, middle note and base note which are different from each other in volatility, characterized in that the whole or a partial amount of the at least one perfume is blended, together with an enzyme, in the form of a precursor, e.g. glycosides or glycerides of a perfume, or amino acid or peptide derivatives of a perfume, which converts into the perfume via decomposition by the action of the enzyme. However, in the aromatic composition proposed in the above publication, immediately after the precursor is blended with the enzyme, the precursor decomposes quickly. Accordingly, it has a drawback that aroma becomes weaker with the passage of time. Furthermore, it has another drawback that when the precursor is stored together with the enzyme as a mixture, for instance before it is used or after a partial amount of it is used, the aforesaid precursor is decomposed and, therefore, the composition is poor in a long time stability. In the aforesaid publication, there is proposed an aromatic agent, bathing agent or detergent which separately comprises a principal agent containing the precursor and a sub-agent containing the enzyme. In a working example, there is described a bathing agent comprising the two agents, where aroma was evaluated only for two hours after the two agents were added to warm water in a bath. Duration of the aroma of two hours might be sufficient for a bathing agent, but is insufficient for other applications. In addition, it is inconvenient to separately prepare and store the two agents and to mix them when they are used. In another working example in the above publication, the perfume derivative was placed in a bottle and lifted by a wick little by little to be vaporized through a vaporizing paper. Alternatively, there is described an aromatic in a gel form, where an enzyme is immobilized in an ager gel together with the aforesaid precursor. However, there is a problem that such a manner of application is inconvenient or their usage is restricted. Various procedures are needed to extract and purify enzymes from organisms. Furthermore, enzymes are unstable after taken out of organisms due to change of environment. For example, enzymes are unstable at or above 5° C. when they are brought into the form of an aqueous solution. As an enzyme solution is unstable particularly at a low concentration, it is necessary to prepare it at a high concentration. However, at a high concentration, there are problems that the enzymes tend to precipitate and offensive odor occurs or bacteria propagate. Accordingly, their applications are restricted to particular types of formulation such as a powder type agent. Enzymes are also unstable particularly to heat.

Meanwhile, the aromatic according to the invention is stable for a long period because it contains neither enzyme nor acid which decomposes the perfume derivatives. In order to emanate aroma, it is enough to apply this aromatic on a proper place where micro-organism is present and, therefore, the aromatic may take any forms such as liquid, powder, gel or aerosol.

The present invention will be further specifically explained below.

A perfume derivative used in the invention is glycosides of perfumes, or phosphate acid ester derivatives of perfumes, amino acid derivatives of perfumes or carboxylic acid derivatives of perfumes which derivatives are decomposed by micro-organisms to release a perfume component. As the aforesaid perfumes, any known perfumes are satisfactorily used. The aforesaid perfume derivatives may be synthesized in known methods.

A sugar part of the glycosides used in the invention may include monosaccharides such as glucose, galactose, mannnose, rhamnose, xylose, ribose, arabinose, glucosamine and galactosamine; and disaccharides such as lactose, maltose, sucrose, cellobiose, isomaltose and epilactose.

The aglycon corresponding to the perfume component in the aforesaid glycoside may include alcohols such as aliphatic alcohols, for example, pentanol, 3-methyl-butanol, 3-methyl-1-pentanol, 2-hexanol, 2-heptanol, undecanol, cis-3-hexenol, cis-6-nonenol, 2,6-nonadiene-1-ol, 9-decenol, geraniol, linalool, nerol, citronellol, hydroxycitronellol, myrcenol, 3,7-dimethyloctanol, farnesol, nerolidol, and lavandulol; cycloaliphatic alcohols, for example, menthol, terpineol, piperitol, perillyl alcohol, carveol, myrtenol, santalol, cedrol, patchouli alcohol, ionol, and hydroxydamascone; aromatic alcohols, for example, benzyl alcohol, cumic alcohol, 2-phenylethyl alcohol, phenylpropyl alcohol, cinnamic alcohol, and α-amylcinnamic alcohol; phenols such as eugenol, vanillin, anisalcohol, raspberry ketone, vanillyl alcohol, piperonyl alcohol, and sesamol; and thiols such as methyl mercaptane, ethyl mercaptane, isopropyl mercaptane, propyl mercaptane, allyl mercaptane, thiogeraniol, thioterpineol, thiolinalool, thiomenthol.

In this specification, the term "aglycon" means the whole non-sugar part which is bound to a sugar part via O-glycoside bond or S-glycoside bond. The bond between aglycon and sugar may be either an α- or β-bond. The glycosides used in the invention may be either an α- or β-form, or a mixture of α- and β-forms. β-Form is preferred because it is easily decomposed by micro-organism, particularly bacteria usually present on the skin.

Many of these glycosides are commercially available with ease. They may also be easily synthesized in known methods. For example, they may be easily synthesized by reacting sugars with the aforesaid alcohols or thiols in the presence of acids. It is possible to synthesize only the β-form using the known Koenigs-Knorr Reaction (Chem. ber., 34,957(1901) ). Alternatively, objective glycosides may be purified by, for example, column chromatography.

The phosphoric acid esters of perfumes used in the invention may include phosphates and pyrophosphates. Alkyl moieties corresponding to a perfume component may include alkyl, alkenyl, alkynyl and aralkyl groups having 5 to 15 carbon atoms which may be branched and may have functional groups such as amyl, nonyl, geranyl, neryl, linalyl, hexenyl, nonadienyl, phenethyl and cinnamyl groups. As a perfume component, use may be made of the same ones as mentioned for the aforesaid glycosides, some of which fall also under the definition given here.

Many of these phosphoric acid ester derivatives are commercially available with ease. They may also be easily synthesized in known methods. For example, they may be easily synthesized from alkyl alcohols or alkyl halogenides and phosphorus oxychloride or diphosphoric esters in accordance with the known method described in J. Org. Chem. 1989, 54, 1338–1342; or Methods. Enzymol., 110,130 (1985).

The amino acid derivatives of perfumes used in the invention may include amino acid esters, N-alkyl amino acids, S-alkyl amino acids and S-oxide alkyl amino acids. An amino acid of which the amino acid derivative is composed may include cystein, alanine, glutamic acid, glycine and phenylalanine. Alkyl moieties corresponding to a perfume component may include alkyl, alkenyl, alkynyl and aralkyl groups having 5 to 15 carbon atoms which may be branched and may have functional groups such as amyl, nonyl, geranyl, neryl, linalyl, hexenyl, nonadienyl, phenethyl and cinnamyl groups. As a perfume component, use may be made of the same ones as mentioned for the aforesaid glycosides, some of which fall also under the definition given here.

The carboxylic acid derivatives of perfumes may include monocarboxylic acid esters and polycarboxylic acid esters. The monocarboxylic acid ester includes quinic acid, caffeic acid, ascorbic acid and glucuronic acid. As a perfume component, use may be made of the same ones as mentioned for the aforesaid glycosides.

Many of the aforesaid amino acid derivatives and monocarboxylic acid derivatives of perfumes are commercially available with ease. They may also be easily synthesized in known methods. For example, they may be easily synthesized from amino acids or carboxylic acids and alcohols or alkyl halogenides in accordance with a process described in "Synthesis and Reactions in Organic Chemistry, New Lecture Series of Experimental Chemistry 14", edited by The Chemical Society of Japan, Maruzen Ltd.

The polycarboxylic acid derivative used in the invention is an ester of a perfume component and a polycarboxylic acid. The polycarboxylic acid includes succinic acid, tartaric acid and citric acid. The polycarboxylic acid group may be those substituted by an ethyl or other group. As a perfume component, use may be made of the same ones as mentioned for the aforesaid glycosides. The polycarboxylic acid derivative in the present invention may be available with ease. They may also be easily synthesized by reacting a polycarboxylic acid with an alcohol corresponding to the perfume component in the presence of an acid. They may also be synthesized by an ester exchange reaction of a lower alkyl ester such as triethyl citrate with the perfume component. If desired, these polycarboxylic acid derivatives may be used after purified by, for example, distillation or column chromatography.

In the prior art, there have been used citric acid monoalkyl esters or trialkyl esters as an emollient agent in cosmetics or triethyl citrate as a diluent for a perfume. These compounds are undesirable as a polycarboxylic acid derivative of a perfume in the present invention because no consideration is paid to substituent groups for aroma.

The perfume derivatives mentioned above may also be obtained as an extract from a natural resource containing the aforesaid perfume derivatives by a process proposed by the present inventors and described in Japanese Patent Application Laid-Open No. Hei-6-057288/94.

The sustained-release aromatic according to the invention may contain at least one of the perfume derivatives mentioned above.

Many of the perfume derivatives used in the invention are soluble in water and, therefore, may be used as an aqueous solution. When their solubility in water is low, they may be used by being solubilized or emulsified, if needed.

A solubilization method for the aforesaid perfume derivatives may include one in which the perfume derivative is dissolved in mono- or polyvalent alcohols, e.g. ethanol, glycerol, propylene glycol, carbitol, diacetin, triacetin, or sorbit, or with a surfactant such as alkylbenzene sulfonic acid salts, higher alcohol sulfuric acid ester salts, alkyltrimethylammonium chlorides, betaines, polyoxyethylene nonylphenyl ether, polyoxyethylene lauryl ether, polyoxyethylenepolyoxypropylene block polymers, or sucrose aliphatic acid esters, and is diluted with water if needed.

An emulsification method for the aforesaid perfume derivatives may include one in which the perfume derivative is homogenized by a colloidal mill or a homogenizer together with a proper amount of an emulsifier, an emulsification stabilizer or a surfactant, such as sucrose aliphatic acid esters, aliphatic acid monoglyceride, sorbitan aliphatic acid esters, propyleneglycol aliphatic acid esters, polyoxyethylene sorbitan aliphatic acid esters, gum arabi, tragacanth gum, methyl cellulose, casein, soybean lecithin, yolk lecithin, starch, sodium alginate, locust bean gum, guar gum, carrageenan, sorbit, propylene glycol, glycerol, xanthan gum, pectin, cellulose derivatives, starch derivatives, cyclodextrin, polyglycerol aliphatic acid esters, saponin, or sucrose.

The sustained-release aromatic according to the invention may take any forms, for example, liquid, powder, gel or aerosol.

A proper excipient such as dextrin, starch or processed starch may be added to the dissolved, solubilized or emulsified perfume derivative, and then the mixture may be dried and powdered by, for example, spray drying or vacuum drying to prepare the sustained-release aromatic.

The aforesaid derivative in a dissolved, solubilized, emulsified or powdered form may be mixed with a proper solvent or carrier and then packed in a vessel with carbon dioxide gas, nitrogen gas or freon gas to prepare a sustained-release aromatic in an aerosol form.

A concentration of the perfume derivative in the sustained-release aromatic of the invention may vary depending on various conditions such as a type of the composition used and a threshold value of the perfume which constitutes the aforesaid perfume derivative and, therefore, shall not be restricted to particular one. In general, the concentration of the perfume derivative is preferably about 0.001 to about 20% by weight, more preferably about 0.005 to about 10% by weight. More specifically, it is preferred to add the perfume derivative in a range of about 0.001 to about 5% by weight in hair cosmetics for human body such as a hair liquid, hair cream or hair mousse, and in a range of about 0.001 to about 10% by weight in skin cosmetics such as a an antiperspirant agent, depending on a site of the skin.

The inventors have conducted researches to find combinations between micro-organisms and the perfume derivatives in which the perfume derivative can be gradually decomposed to emit aroma over a long time.

Bacteria usually present on the skin are usually found on, for example, the skin, head skin or hair of human beings or animals, or on the surface of fiber products such as clothes, e.g. under wears or socks. Examples of the bacteria include *Staphylococcus epidermidis*, *Propionibacterium acnes*, Coryneform bacteria (aerobic dephtheroids), *Staphylococcus aureus*, Ptyrococcus sp., and Micrococcus sp.

The present inventors have noted that axillary odor which is a main cause of unpleasant odor on a human body is produced by decomposition of fluid secreted from the apocrine gland with Corynebacterium which is usually present on the axillary fossa, and have searched for perfume derivatives which are decomposed by bacteria such as Coryneform bacteria to emit aroma. As a result, it has been found that it is preferred in the case of Coryneform bacteria to blend a perfume glycoside, preferably one in which a perfume component is bound to sugar in β-bonding, particularly in a sustained-release aromatic for an antiperspirant agent. It has not been known in the prior art that Corynebacterium, which is one of the bacteria usually present on the skin and concerned with axillary odor, stably causes aroma from, for example, a perfume glycoside having β-bonding, which has been found first by the present inventors. In addition, it has also been found first by the present inventors that other bacteria usually present on the skin stably cause aroma from a perfume glycoside.

The aforesaid yeast is not restricted to particular ones. Use may be made of, for example, ones belong to Endomycetales such as Saccharomyces, Hansenula, Kluyveromyces, Lodderomyces, Pichia, Nadsonia, Saccharomycodes, Hanseeniaspora, Schizosaccharomyces, Lipomyces, Endomycopsis and Nematospora; ones belong to Ustilaginales such as Leucosporidium and Rhodosporidium; ones belong to Sporobolomycetaceae such as Bullera, Sporoboromyces and Sporidiobolus, [all of the above are called Ascomycotina yeast]; Brettanomyces, Crytococcus, Kloeckera, Rhodotorula and Sterigmatomyces, which are called non-spore yeast, with *Saccharomyces cerevesiae* being particularly preferred because of its low cost, availability and easy handling.

As the micro-organism in the present invention, preference is given to bacteria usually present on the skin and yeast. As the aforesaid perfume derivative, preference is given to a perfume glycoside, particularly a glycoside in which a perfume component is bound to sugar in β-bonding.

The sustained-release aromatic according to the invention is used to mask various odors released from, for example, the skin, head skin or hair of human or animal bodies, or to wear pleasant aroma actively. It's applications are not restricted to particular ones. Examples of the present aromatic used for human body may include hair cosmetics such as hair liquids, hair mousses, hair rinses, hair conditioners, pomades, and hair glowen; liquid or powdery anti-perspirant agents; baby powder; deodorant spray for body; foot spray; body cleaners for nursing; and wet tissues. For animals, it may be applied in animal care agents such as deodorants, shampoos or rinses. In addition, cloths to touch the skin, for example, underwears, shirts, socks, shoes, various sanitary goods, and bandages may be made to emit aroma when used by impregnating or smearing them with the sustained-release aromatic of the invention. In addition, as bacteria usually present on the skin are present on the clothes which are once worn the clothes may emit aroma in a non-wearing state after a detergent, rinse agent or finishing agent in which the sustained-release aromatic of the invention is blended is applied to them by impregnation or smearing.

Other applications of the sustained-release aromatic of the invention include such where it is added in drinks or foods containing yeast, which may then emit aroma in a fermentation step. Thus, it is possible to confirm a degree of fermentation and, further, to reduce a loss of aroma, compared to the case where an aromatic is added before fermentation.

The sustained-release aromatic of the invention may also be used as a detecting indicator for confirming the presence of micro-organisms such as bacteria usually present on the skin and yeast, taking advantage of release of the perfume component with micro-organisms.

In the sustained-release aromatic of the invention, conventional materials may be added in addition to the aforesaid perfume derivatives, such as natural oils such as peppermint oil, spearmint oil, rose oil, patchouli oil, orange oil, neroli oil, and lemon oil; terpene type hydrocarbons such as α-pinene, β-pinene, terpinolene, and p-cymene; aliphatic alcohols such as cis-3-hexenol, n-undecylenic alcohol, and n-octhyl alcohol; terpene type alcohols such as linalool, geraniol, citroneliol, 1-menthol, nerolidol, and santalol; aromatic alcohols or derivatives thereof such as phenylethyl alcohol, cinnamic alcohol, methylphenyl carbinol, and t-buthyl cyclohexanol; phenols or derivatives thereof such as anisole, anethole, and eugenol; aliphatic aldehydes such as n-heptyl aldehyde, undecylenic aldehyde, and 2,6-nonadienal; terpene type aldehydes such as citral, citronellal, hydroxy citronellal, and perillaldehyde; aromatic aldehydes such as benzaldehyde, phenylacetaldehyde, cinnamic aldehyde, anisaldehyde, cuminaldehyde, heliotropine, cyclamenaldehyde, and vanillin; aliphatic ketones such as methyl n-amyl ketone, methyl heptenone, and diacetyl; terpene type cyclic ketones such as 1-carvone, menthone, piperitone, and camphor; cyclic ketones such as benzophenone, ionone, methylionone, irone, maltol, and jasmone; musk type perfume compounds such as large cyclic musks, e.g. muscone, cyclopentadecanone, and ethylene brassylate, nitro musk, and indan musk; oxides such as rose oxide, and linalool oxide; esters of aliphatic or aromatic acids and alcohols such as terpene alcohols, aliphatic alcohols, aromatic alcohols or phenols; nitrogen-containing perfume compounds; sulfur-containing perfume compounds; and blended perfumes in which two or more of these exemplified natural oils or perfume compounds are mixed.

In addition to the aforesaid compounds, the following materials may be added in the sustained-release aromatic of the invention: anti-perspirant agents such as aluminum chlorohydroxide(ACH); disinfectants such as 3,4,4'-trichlorocarbanilide (TCC); deodorants such as lauryl methacrylate, geranyl crotonate and flavonoid; pigments; and any other materials.

It is possible to add other types of perfumes than the perfume components of the perfume derivatives to the sustained-release aromatic of the invention in addition to the aforesaid perfume derivatives to vary aroma between a time before or just after the application and a time when the aromatic is being used. Thus, a change in aroma with the passage of time may be attained.

The present invention will be elucidated more specifically with reference to the following Examples.

SYNTHESIS EXAMPLES

Synthesis Example 1

Process for the Synthesis of 2-Phenylethyl Glucoside (βform)

A solution of 40 g of acetobromoglucose in 100 ml of dry ether was added dropwise to a mixture of 125 g of molecular sieves 4A as a dehydrating agent, 30.8 g of silver(I) trifluoroacetate and 300 ml of dry ether while cooling the mixture with iced water, to which a solution of 12.2 g of β-phenylethyl alcohol in 30 ml of dry ether was then added dropwise. Reaction was then carried out at room temperature for 8 hours. After the end of the reaction, ethyl acetate was added to the reaction liquid. The reaction liquid was filtered through celite and the filtrate was washed with an aqueous solution of sodium bicarbonate. After an oily layer was dehydrated, it was concentrated under reduced pressure to obtain a crude product, tetraacetyl derivative of 2-phenylethyl glucoside. The tetracetyl derivative was purified on a silica gel column. The tetraacetyl derivative was deacetylated with sodium methylate(NaOMe) in 300 ml of methanol at room temperature and purified with column chromatography to obtain 15.3 g of the intended product. According to $^{13}$C-NMR on the crystals obtained, a signal of C-1 position was detected at 102.0 ppm. It was, therefore, confirmed that the product had a β-bonding.

Synthesis Example 2

Process for the Synthesis of 2-Phenylethyl Glucoside (α-form)

A mixture of 40 g of D-glucose, 240 g of 2-phenylethyl alcohol and 8 g of an acidic ion exchange resin (amberlist 15) was subjected to reaction at 80 to 85° C. for 8 hours. After the end of the reaction, the reaction liquid was cooled to room temperature and then filtered through celite. An excess amount of 2-phenylethyl alcohol was removed from the mother liquor under reduced pressure. A three-fold volume of water was added to the crude product obtained, and was placed in a refrigerator. Then, 20 g of 2-phenylethyl glucoside (α-form) was obtained as white crystals. According to $^{13}$C-NMR, a signal of C-1 position was detected at 97.7 ppm. It was, therefore, confirmed that the product had an α-bonding.

Synthesis Example 3

Process for the Synthesis of Glucovanillin (β-form)

A solution of 5.0 g of vanillin in 1N potassium hydroxide/ethanol was added dropwise to a solution of 16 g of acetobromoglucose dissolved in 50 ml of dry chloroform. The mixture was stirred under reflux conditions for one hour and then cooled to room temperature. After the inorganic salts precipitated were filtered off, the mother liquor was washed with pure water. A chloroform layer was dehydrated and then concentrated under reduced pressure. The tetraacetyl derivative obtained was purified on a silica gel column. The tetraacetyl derivative was deacetylated with 50 ml of methanol and sodium methylate at room temperature and then purified with column chromatography to obtain 3.5 g of the intended product. According to $^{13}$C-NMR of the crystals obtained, a signal of C-1 position was detected at 99.8 ppm. It was, therefore, confirmed that the product had a β-bonding.

Synthesis Example 4

Process for the Synthesis of Citronellyl Glucoside (β-form)

A solution of 40 g of acetobromoglucose in 100 ml of dry ether was added dropwise to a mixture of 125 g of molecular sieves 4A as a dehydrating agent, 30.8 g of silver(I) trifluoroacetate and 300 ml of dry ether while cooling the mixture with iced water, to which a solution of 12.2 g of citronellol in 30 ml of dry ether was then added dropise. Reaction was then carried out at room temperature for 8 hours. After the end of the reaction, ethyl acetate was added to the reaction liquid. The reaction liquid was filtered through celite and the filtrate was washed with an aqueous solution of sodium bicarbonate. After an oily layer was dehydrated, it was concentrated under reduced pressure. The tetraacetyl derivative thus obtained was purified on a silica gel column. The tetraacetyl derivative was deacetylated with 300 ml of methanol and sodium methylate at room temperature and purified with column chromatography to obtain 15.3 g of the intended product. According to $^{13}$C-NMR of the crystals obtained, a signal of C-1 position was detected at 104.3 ppm. It was, therefore, confirmed that the product had a β-bonding.

Synthesis Example 5

Process for the Synthesis of Eugenyl Glucoside (β-form)

8.0 g of glucose pentaacetate were dissolved in 40 ml of absolute toluene, to which 3.28 g of eugenol and 2.0 g of molecular sieves 4A were then added. The mixture was stirred for about one hour. Next, 1 ml of a boron trifluoridediethyl ether complex was added to the mixture. Stirring was further continued for a day and night. After the end of the reaction, molecular sieves 4A was filtered off. The filtrate was washed twice with each 50 ml of a 0.5N aqueous solution of potassium hydroxide to remove unreacted eugenol. After washed further with water and dried with sodium sulfate, it was dried under reduced pressure to obtain 2.4 g of the intended product. According to $^{13}$C-NMR of the crystals obtained, a signal of C-1 position was detected at 102.9 ppm. It was, therefore, confirmed that the product had a β-bonding.

Synthesis Example 6

Process for the Synthesis of Sodium 2-Phenylethyl Phosphate 46.0 g of phosphorus oxychloride were added dropwise to 36.7 g of β-phenylethyl alcohol at room temperature. Reaction was conducted at room temperature for 5 hours, and the reaction liquid was poured in 500 ml of cold water and then the reaction was further continued for 5 hours. Ether was added to the reaction mixture for extraction. The extract was concentrated and reacted with 22.5 g of NaOH and 600 ml of ethanol. Then, 500 ml of toluene and 50 ml of methanol were added to the mixture. Precipitates were filtered to obtain 60 g of the intended product. Its structure was confirmed with $^{13}$C-NMR.

Synthesis Example 7

Process for the Synthesis of Isopropyl Thiogalactoside 43 g of tin tetrachloride were added dropwise to a solution of 65 g of isopropyl thiotributyline, 50 g of pentaacetylgalactose and 300 ml of dichloroethane while cooling the mixture with iced water. Reaction was conducted at room temperature for 3 hours, and the reaction liquid was poured in a KF solution. The Crystals precipitated were filtered off. The filtrate was washed with an aqueous solution of sodium bicarbonate, dehydrated and concentrated to obtain a tetracetyl derivative. This was deacetylated with NaOMe in 400 ml of methanol to obtain 24 g of the intended product. The structure was confirmed with $^{13}$C-NMR.

Synthesis Example 8

Synthesis of a Quinic Acid 9-Decenyl Ester 23.0 g of a quinic acid potassium salt were reacted with 13.8 g of 9-decenyl chloride in 200 ml of N,N-dimethylformamide at 100° C. for 4 hours. After the end of the reaction, N,N-dimethylformamide was recovered under reduced pressure. Methanol was added to the reaction mixture and undissolved materials were removed with filtration.

Methanol was recovered under reduced pressure to obtain 31.3 g of the intended product. The structure was confirmed with $^{13}$C-NMR.

Synthesis Example 9

Synthesis of Raspberry Ketone Glucoside 13 g (0.07 mole) of boron trifluoride acetic acid were added to a mixture of 46 g (0.28 mole) of raspberry ketone, 109 g (0.28 mole) of pentaacetyl glucose and 525 ml of absolute toluene. Stirring was continued at room temperature for 7 hours. The reaction liquid was poured in water, to which ethyl acetate was added to separate phases. The organic layer was washed twice with 5% NaOH aqueous solution and once with saturated brine. After the solvent was removed under reduced pressure, recrystallization was conducted in ethanol to obtain 81 g of raspberry ketone-tetraacetyl glucoside (yield of 59%). The raspberry ketone-tetraacetyl glucoside obtained was deacetylated with sodium methoxide according to the known manner and then neutralized with an ion exchange resin (amberlite). After the ion exchange resin was filtered off, the solvent was removed under reduced pressure to obtain 48 g of raspberry ketone glucoside (β-form). The structure was confirmed with $^{13}$C-NMR.

Synthesis Example 10

Synthesis of cis-3-Hexenyl Glucoside

A mixture of 40 g of D-glucose, 150 g of cis-3-hexenol and 8 g of an acidic ion exchange resin (amberlist 15) was subjected to reaction at 80 to 85° C. for 8 hours. After the end of the reaction, the reaction liquid was cooled and then filtered through celite. An excess amount of cis-3-hexenol was removed from the mother liquor under reduced pressure. After cis-3-hexenol-glucoside which remained was removed with silica gel column chromatography (developing solvent, chloroform/methanol=8/1), a cis-3-hexenyl glucoside fraction was concentrated under reduced pressure to obtain the objective cis-3-hexenyl glucoside. It was confirmed with $^{13}$C-NMR that the product contained α- and β-forms in a ratio of α-form: β-form=7:3.

Synthesis Example 11

Process for the Synthesis of a Citric Acid Phenylethyl Ester Derivative (Hereinafter Referred to as CAPE)

After 300 mg of potassium carbonate were added to 10 g of triethyl citrate and 13.3 g of phenylethyl alcohol, stirring was continued under heating for 6 hours while removing ethanol formed. After the end of the reaction, an ether layer was washed with 50 ml of diethyl ether and with 50 ml of purified water. The ether layer was dried with magnesium sulfide and then concentrated under reduced pressure. Distillation under reduced pressure was further carried out to remove unreacted phenylethyl alcohol and triethyl citrate. As a bottom residue after the distillation, 7.4 g of a citric acid phenylethyl ester derivative were obtained. According to a GC-MS analysis, it was confirmed the production of monophenylethyldiethyl citrate and diphenylethylmonoethyl citrate.

Synthesis Example 12

Process for the Synthesis of a Citric Acid Rose Base Ester Derivative (Hereinafter Referred to as CARE)

The same procedure was conducted as in Synthesis Example 11, except that 10 g of rose base having the formulation shown in Table 1 was used in place of phenylethyl alcohol. As a bottom residue after the distillation, 6.8 g of a citric acid rose base ester derivative were obtained.

TABLE 1

| component | amount, wt. % |
| --- | --- |
| citronellol | 16.0 |
| benzyl alcohol | 5.0 |
| 9-decene-1-ol | 3.0 |
| nonanol | 1.0 |

Example 1

Glycoside Decomposition Ability Test of Coryneform Bacteria (Corynebacterium)

Each of the glycosides synthesized in Synthesis Examples 1 to 3 was added to a soybean casein digest liquid medium (SCD liquid medium) at an amount of 0.5% by weight based on the medium. To the liquid medium was inoculated 2% of bacterial liquid of Coryneform bacteria which had been precultured in an SCD liquid medium. This was cultured at 32° C. in a static state. The culture liquid was sampled after 2 days and 4 days culture and sterizing treatment was conducted on a conventional manner. After the sterizing treatment, aroma components were extracted with the same volume of diethyl ether as that of the culture liquid sampled. The structure of the components was identified on a GC-MS. The amount of the components released was determined on a GC with a detector of FID. The results are as shown in Tables 2 and 3.

TABLE 2

| | Detected component and its amount 2-phenylethyl alcohol (peak area × 10$^6$) | |
| --- | --- | --- |
| | after 2 days culture | after 4 days culture |
| 2-phenylethylglucoside (β-form) from Synthesis Example 1 | 1.1 | 8.0 |
| 2-phenylethylglucoside (α-form) from Synthesis Example 2 | 0.01 | 0.3 |

TABLE 3

| | Detected component and its amount (peak area × 10$^6$) | | | |
| --- | --- | --- | --- | --- |
| | vanillin | | vanillyl alcohol | |
| | after 2 days culture | after 4 days culture | after 2 days culture | after 4 days culture |
| glucovanillin (β-form) from Synthesis Example 3 | 0.01 | 1.75 | 0 | 0.2 |

As seen from Table 2, the detected amount of 2-phenylethyl alcohol released from the β-form was higher than that from the α-form. As seen from Table 3, vanillyl alcohol as well as vanillin was detected in glucovanillin (β-form).

Example 2

Perfume Glycoside Decomposition Ability Test of Bread Yeast (*Saccharomyces Cerevesiae*)

*Saccharomyces cerevesiae* which had been cultured at 30° C. for 1 hour was added, at a concentration of 7% by weight, to a 15% by weight sucrose aqueous solution each containing the glycosides prepared in Synthesis Examples 2, 4 or 5 in an amount of 0.5% by weight. This was cultured at 4° C. while shaked. After 15 minutes and 4 hours culture, the culture liquid was sampled and centrifuged to precipitate the yeast. The supernatant was then extracted with the same volume of diethyl ether as that of the supernatant. The structure of the aroma components was identified on a GC-MS. The amount of the component released was determined on a GC with a detector of FID. The results are as shown in Table 4.

TABLE 4

| Perfume glycoside | Amount of aroma components (peak area × 10$^5$) | |
|---|---|---|
| | after 15 minutes culture | after 4 hours culture |
| citronellyl glucoside (β-form) | 2.6 | 8.8 |
| 2-phenylethyl glucoside (α-form) | 0.4 | 1.6 |
| eugenyl glucoside (β-form) | 0.5 | 1.3 |

Citronellol was identified as an aroma component released from citronellyl glucoside (β-form); 2-phenylethyl alcohol from 2-phenylethyl glucoside (α-form); and eugenol from eugenyl glucoside (β-form).

Examples 3 and 4 and Comparison Examples 1 and 2 (Hair Tonic)

Hair tonics were prepared with the formulations as indicated in Table 5 and evaluated. The values are represented in percent by weight.

TABLE 5

| | Ex. 3 | Ex. 4 | Comp. Ex. 1 | Comp. Ex. 2 |
|---|---|---|---|---|
| Ethanol | 55.0 | 55.0 | 55.0 | 55.0 |
| Polyoxy ethylene(20) polyoxypropylene(20) | 0.1 | 0.1 | 0.1 | 0.1 |
| Alkyl ether pyridoxine | 0.05 | 0.05 | 0.05 | 0.05 |
| 1,3-butylene glycol | 2.0 | 2.0 | 2.0 | 2.0 |
| Purified water | balance | balance | balance | balance |
| 2-phenylethyl alcohol (MW 122) | — | — | 0.48 | — |
| 2-phenylethyl glucoside (β-form, MW 284) (Synthesis Example 1) | 1.12 | — | — | — |
| vanillin (MW 152) | — | — | — | 0.3 |
| Glucovanillin (β-form, MW 314) (Synthesis Example 3) | — | 0.62 | — | — |

Two subjects, 24 and 37 years old men, were treated with a shampoo which did not contain any perfume and then provided on either side of their heads with the hair tonics prepared in the Examples and Comparison Examples. Intensity of aroma on the applied parts was evaluated just after the application, one hour, 8 hours and 1 day after the application by two skilled panels. The evaluation standards indicated below were used in this sensuous test. The results are as shown in Table 6.

TABLE 6

| subject | Ex. 3 | | Ex. 4 | | Comp. Ex. 1 | | Comp. Ex. 2 | |
|---|---|---|---|---|---|---|---|---|
| | A | B | A | B | A | B | A | B |
| just after the application | — | — | — | — | +++ | +++ | +++ | +++ |
| 1 hour after the application | — | — | — | — | ++ | ++ | +++ | +++ |
| 8 hours after the application | + | + | + | + | — | — | ++ | ++ |
| 1 day after the application | + | + | + | + | — | — | ++ | ++ |

+++ too strong
++ strong
+ good
− weak
— no aroma

As seen from the results indicated above, in the cases where a conventional perfume components, 2-phenylethyl alcohol and vanillin were applied, the aroma was too strong or remained less. Thus, preferable aroma over a long time was not obtained in these cases. Meanwhile, it is apparent that in the cases of the present aromatic, comfortable aroma continued for a long time.

Examples 5 and 6 and Comparison Example 3 (Powdery Spray of an Antiperspirant Agent)

Powdery sprays of a sweat-suppressing agent were prepared with the formulation indicated in Table 7. The values are indicated in percent by weight.

TABLE 7

| Component | Example | | Comparison Example |
|---|---|---|---|
| | 5 | 6 | 3 |
| Rehydrol | 10.0 | 10.0 | 10.0 |
| isopropylmethylphenol | 0.5 | 0.5 | 0.5 |
| isopropyl myristate | 5.0 | 5.0 | 5.0 |
| POE alkylphenyl ether phosphate | 3.0 | 3.0 | 3.0 |
| perfume (citrus musk type) | 0.3 | 0.3 | 0.3 |
| absolute ethanol | balance | balance | balance |
| glucovanillin (β-form) from Synthesis Example 3 | 0.1 | — | — |
| raspberry ketone glucoside (β-form) from Synthesis Example 9 | — | 0.5 | — |

Axillary fossae of ten subjects, 24 to 45 years old men, were treated with a body shampoo and provided on each side with each of cosmetics prepared in the Example and the Comparison Example. Intensity of the remaining aroma and unpleasant odor,i.e. axillary odor, on the subjects were evaluated by comparing the oders from both fossae, 3 hours, 8 hours and 1 day after the application by two skilled panels. The results are represented by the number of subjects whose remaining aroma was judged to be strong and the number of subjects whose body odor was judged to be masked. The results are as shown in Table 8.

TABLE 8

| | aroma remaining | | | level of masking | | |
|---|---|---|---|---|---|---|
| | Ex. 5 | Ex. 6 | Comp. Ex. 3 | Ex. 5 | Ex. 6 | Comp. Ex. 3 |
| 3 hours after the application | 10 | 10 | 10 | 10 | 10 | 10 |

TABLE 8-continued

| | aroma remaining | | | level of masking | | |
|---|---|---|---|---|---|---|
| | Ex. 5 | Ex. 6 | Comp. Ex. 3 | Ex. 5 | Ex. 6 | Comp. Ex. 3 |
| 8 hours after the application | 9 | 10 | 1 | 10 | 10 | 10 |
| 1 day after the application | 10 | 10 | 0 | 10 | 10 | 0 |

As seen from Table 8, the remaining aroma continued until one day after the application in both Examples 5 and 6, while it could be sensed very little 8 hours after the application in Comparison Example 3. The high level of masking continued until one day after the application both Examples 5 and 6. Meanwhile, in Comparison Example 3, the masking effect was detected until 8 hours after the application, but completely lost one day after.

Example 7 and Comparison Example 4

(Hair Tonic)

Hair tonics were prepared with the formulations indicated in Table 9 below.

TABLE 9

| Component | Ex. 7 | Comp. Ex. 4 |
|---|---|---|
| ethanol | 55.0 | 55.0 |
| polyoxyethylene(20)polyoxypropylene(20) alkyl ether | 0.1 | 0.1 |
| pyridoxine | 0.05 | 0.05 |
| disinfectant | 0.1 | 0.1 |
| methylparaben | 0.1 | 0.1 |
| 1,3-butylene glycol | 2.0 | 2.0 |
| purified water | balance | balance |
| perfume (citrus type) | 0.2 | 0.3 |
| c-3-hexenylglucoside (α-form: β-form = 7:3) from Synthesis Example 10 | 0.1 | — |

Example 8 and Comparison Example 5

(Body Powder)

Body powder were prepared with the formulations indicated in Table 10 below.

TABLE 10

| Component | Ex. 8 | Comp. Ex. 5 |
|---|---|---|
| magnesium bicarbonate | 4.0 | 4.0 |
| kaolin | 4.0 | 4.0 |
| talc | 88.6 | 88.6 |
| zinc oxide | 3.0 | 3.0 |
| antiseptic | 0.1 | 0.1 |
| perfume (rose floral type) | 0.25 | 0.3 |
| 2-phenylethylglucoside (β-form) from Synthesis Example 1 | 0.04 | — |
| isopropylthiogalactoside from Synthesis Example 7 | 0.01 | — |

Example 9 and Comparison Example 6

(Wet Tissue Composition)

Wet tissue composition were prepared with the formulations indicated in Table 11 below.

TABLE 11

| Component | Ex. 9 | Comp. Ex. 6 |
|---|---|---|
| ethanol | 54.0 | 54.0 |
| aluminum chlorohydroxide | 0.7 | 0.7 |
| benzalkonium chloride | 0.1 | 0.1 |
| perfume (powdery floral type) | 0.15 | 0.3 |
| sodium 2-phenylethyl phosphate from Synthesis Example 6 | 0.10 | — |
| quinic acid 9-decenyl ester from Synthesis Example 8 | 0.05 | — |
| purified water | balance | balance |

Ten subjects, 24 to 45 years old men, were treated with a shampoo or a body shampoo and provided on either side with each of the cosmetics prepared in Examples 7 to 9 and Comparison Examples 4 to 6. Intensity of the remaining aroma and intensity of their head skin odor and their body odor on the applied parts were evaluated 1 hour, 8 hours and 1 day after the application by two skilled panel by comparing the right and left sides. The results are represented by the number of persons whose remaining aroma was judged to be strong and the number of persons whose head skin odor or body odor was judged to be unpleasant. The results are as shown in Table 12.

TABLE 12

| Evaluation | Ex. 7 | Ex. 8 | Ex. 9 | Comp. Ex. 4 | Comp. Ex. 5 | Comp. Ex. 6 |
|---|---|---|---|---|---|---|
| Aroma remaining | | | | | | |
| 1 hour after the application | 0 | 0 | 0 | 10 | 10 | 10 |
| 8 hours after the application | 9 | 10 | 10 | 1 | 0 | 0 |
| 1 day after the application | 10 | 10 | 10 | 0 | 0 | 0 |
| head skin odor | | | | | | |
| 1 hour after the application | 0 | — | — | 0 | — | — |
| 8 hours after the application | 0 | — | — | 6 | — | — |
| 1 day after the application | 1 | — | — | 10 | — | — |
| body odor | | | | | | |
| 1 hour after the application | — | 0 | 0 | — | 0 | 0 |
| 8 hours after the application | — | 0 | 0 | — | 4 | 5 |
| 1 day after the application | — | 2 | 3 | — | 10 | 10 |

As seen from Table 12, the evaluations in the Examples were better than those in the Comparison Examples in all items.

Examples 10 and 11 and Comparison Example 7

(Hair Tonic)

Hair tonics were prepared with formulations indicated in Table 13 and evaluated.

TABLE 13

| component, wt. % | Ex. 10 | Ex. 11 | Comp. Ex. 7 |
|---|---|---|---|
| ethanol | 55.0 | 55.0 | 55.0 |
| polyoxyethylene(20)polyoxy-propylene(20) alkyl ether | 0.1 | 0.1 | 0.1 |
| pyridoxine | 0.05 | 0.05 | 0.05 |

TABLE 13-continued

| component, wt. % | Ex. 10 | Ex. 11 | Comp. Ex. 7 |
| --- | --- | --- | --- |
| disinfectant | 0.1 | 0.1 | 0.1 |
| methylparaben | 0.1 | 0.1 | 0.1 |
| 1,3-butylene glycol | 2.0 | 2.0 | 2.0 |
| purified water | balance | balance | balance |
| CAPE (Synthesis Example 11) | 0.3 | — | — |
| CARE (Synthesis Example 12) | — | 0.5 | — |
| perfume (floral musk type) | 0.2 | 0.2 | 0.2 |

Ten subjects, 24 to 45 years old men, were treated with a shampoo which did not contain any perfume and provided on either side of their heads with the hair tonics prepared in Examples 10 and 11 and Comparison Example 7. Intensity of the remaining aroma 3 hours, 8 hours and 1 day after the application was evaluated by the two skilled panels and represented in the number of subjects. The results are as shown in Table 14.

TABLE 14

| | Intensity of aroma | | |
| --- | --- | --- | --- |
| | Ex.10 | Ex. 11 | Comp. Ex. 7 |
| 3 hours after the application | 10 | 10 | 10 |
| 8 hours after the application | 9 | 10 | 1 |
| 1 day after the application | 10 | 10 | 0 |

As seen from Table 14, the aroma was sensed until 1 day after the application in the Examples, while almost no aroma was sensed 8 hours after the application in the Comparison Example.

Industrial Applicability

The sustained-release aromatic of the present invention itself has only very weak aroma and, therefore, meets consumer's preference to less aroma or no aroma. As the present aromatic releases a perfume component only when it is decomposed by micro-organisms such as bacteria usually present on the skin or yeast, the amount of perfumes to be used can be reduced, compared to sustained-release aromatics of the prior art which tend to contain a more amount of perfumes than needed in order to keep the intensity of aroma over a long time. The stability with the passage of time of the sustained-release aromatic of the present invention is also much better than that of the prior art because the perfume component is contained in the form of derivative. The sustained-release aromatic composition of the present invention is excellent in keeping and increasing aroma, and moreover, is unique in that when it is used in a blend perfume, the perfume exhibit aroma which varies with time. The sustained-release aromatic composition of the present invention is useful for applications on the skin, head skin or hair of human beings or animals, on clothes, or in drinks and foods, or as an indicator for detecting microorganisms.

What is claimed is:

1. A method for producing an aroma from a perfume derivative which does not contain an enzyme or an acid that releases a perfume component, said method comprising applying the perfume derivative on the skin of a subject such that a microorganism that is present on the skin releases the perfume component from the perfume derivative thereby producing the aroma, wherein the perfume derivative is selected from the group consisting of a glycoside of perfume, a phosphoric acid ester derivative of perfume, an amino acid derivative of perfume, and a mixture thereof.

2. The method of claim 1, wherein the perfume derivative is present in an anti-perspirant agent.

3. The method of claim 1, wherein the perfume derivative is present in a hair cosmetic.

4. The method of claim 1, wherein the perfume component comprises an alcohol or a thiol.

5. The method of claim 4, wherein the alcohol comprises an aliphatic alcohol, a cycloaliphatic alcohol, an aromatic alcohol, or a phenol derivative.

6. The method of claim 4, wherein the alcohol comprises pentanol, 3-methyl-butanol, 3-methyl-1-pentanol, 2-hexanol, 2-heptanol, undecanol, cis-3-hexenol, cis-6-nonenol, 2,6-nonadiene-1-ol, 9-decenol, geraniol, linalool, nerol, citronellol, hydroxycitronellol, myrcenol, 3,7-dimethyloctanol, farnesol, nerolidol, lavandulol, menthol, terpineol, piperitol, perillyl alcohol, carveol, myrtenol, santalol, cedrol, patchouli alcohol, ionol, hydroxydamascone, benzyl alcohol, cumic alcohol, 2-phenylethyl alcohol, phenylpropyl alcohol, cinnamic alcohol, a-amylcinnamic alcohol, eugenol, vanillin, anisalcohol, raspberry ketone, vanillyl alcohol, piperonyl alcohol, sesamol, methyl mercaptane, ethyl mercaptane, isopropyl mercaptane, propyl mercaptane, allyl mercaptane, thiogeraniol, thioterpineol, thiolinalool, or thiomenthol.

7. The method of claim 1, wherein a sugar part of the glycoside of perfume comprises glucose, galactose, mannose, rhamnose, xylose, ribose, arabinose, glucosamine, galactosamine, lactose, maltose, sucrose, cellobiose, isomaltose or epilactose.

8. The method of claim 1, wherein the phosphoric acid ester derivative of the perfume comprises a phosphate derivative of perfume or pyrophosphate derivative of perfume.

9. The method of claim 1, wherein an amino acid component of the amino acid derivative of perfume comprises a cystein derivative, an alanine derivative, a glutamic acid derivative, a glycine derivative, or a phenylalanine derivative.

10. The method of claim 1, wherein the microorganism is bacteria or yeast.

11. A method for releasing a perfume component of a perfume derivative which does not contain an enzyme or an acid that releases the perfume component, said method comprising applying the perfume derivative on the skin of a subject such that a microorganism that is present on the skin releases the perfume component from the perfume derivative, wherein the perfume derivative is selected from the group consisting of a glycoside of perfume, a phosphoric acid ester derivative of perfume, an amino acid derivative of perfume, and a mixture thereof.

12. The method of claim 11, wherein the perfume derivative is a component of an antiperspirant agent.

13. The method of claim 11, wherein the perfume derivative is a component of a hair cosmetic.

14. A method for producing a sustained aroma from the skin of a subject comprising applying a perfume derivative on the skin of a subject such that a microorganism that is present on the skin releases the perfume component from the perfume derivative thereby producing the aroma, wherein the perfume derivative is selected from the group consisting of a glycoside of perfume, a phosphoric acid ester derivative of perfume, an amino acid derivative of perfume, and a mixture thereof, and wherein the perfume derivative does not contain an enzyme or an acid that releases a perfume component.

15. The method of claim 14, wherein the sustained aroma is produced from an antiperspirant agent which comprises the perfume derivative.

16. The method of claim 14, wherein the sustained aroma is produced from a hair cosmetic which comprises the perfume derivative.

* * * * *

Disclaimer

6,576,247—Takeshi Ikemoto, Kanagawa; Hiroko Nakatsugawa, Kanagawa; Bun-ichi Okabe, Kanagawa; Kazuo Ogino, Tokyo; Jun-ichi Matsui, Kanagawa; Minoru Iwamoto, Kanagawa; Akira Fujita, Kanagawa; Masayoshi Inui, Kanagawa, all of Japan. SUSTAINED-RELEASE AREOMATIC AND METHOD OF DETECTING MICRO-ORGANISM BY USING THE SAME. Patent dated June 10, 2003. Disclaimer filed July 26, 2004, by assignee, Kanebo Ltd. And T. Hasegawa Co. Ltd.

This patent is subject to a terminal disclaimer.

*(Official Gazette, July 26, 2005)*